United States Patent
Sofranko et al.

(10) Patent No.: US 11,046,625 B1
(45) Date of Patent: Jun. 29, 2021

(54) REACTOR FOR OXIDATIVE CONVERSION OF HYDROCARBON FEEDS

(71) Applicant: Bio2Electric, LLC, Woburn, MA (US)

(72) Inventors: John A. Sofranko, Weston, MA (US); Elena Y. Chung, Somerville, MA (US); William K. Wang, Woburn, MA (US)

(73) Assignee: EcoCatalytic Inc., Woburn, MA (US)

( * ) Notice: Subject to any disclaimer, the term of this patent is extended or adjusted under 35 U.S.C. 154(b) by 0 days.

(21) Appl. No.: 16/888,066

(22) Filed: May 29, 2020

Related U.S. Application Data

(60) Provisional application No. 62/853,887, filed on May 29, 2019.

(51) Int. Cl.
*C07C 5/00* (2006.01)
*C07C 5/32* (2006.01)
(Continued)

(52) U.S. Cl.
CPC .............. *C07C 5/322* (2013.01); *B01J 8/005* (2013.01); *B01J 38/30* (2013.01); *C07C 4/025* (2013.01);
(Continued)

(58) Field of Classification Search
CPC .. C07C 5/48; C07C 11/04; C07C 2/84; C07C 11/06; C07C 2521/02; C07C 2521/04;
(Continued)

(56) References Cited

U.S. PATENT DOCUMENTS

| 2,493,038 A | 1/1950 | Snyder et al. |
| 3,651,121 A | 3/1972 | Duke et al. |

(Continued)

FOREIGN PATENT DOCUMENTS

| EP | 2576046 B1 | 11/2014 |
| EP | 2853521 A1 | 4/2015 |

(Continued)

OTHER PUBLICATIONS

Sofranko et al., "Natural Gas to Gasoline: the ARCO GTG Process", Symposium on Methane Activation, Conversion and Utilization, International Congress of Pacific Basin Societes, Dec. 17-20, 1989, pp. 152.154.
(Continued)

*Primary Examiner* — Sharon Pregler
(74) *Attorney, Agent, or Firm* — RatnerPrestia

(57) ABSTRACT

A system for oxidative conversion of a mixed hydrocarbon feed stream to a product stream containing at least one olefin is provided. The system includes a plurality of reactors each capable of oxidatively dehydrogenating at least a portion of a hydrocarbon in the mixed hydrocarbon feed, and each reactor able to operate at different set of reaction conditions from other reactors in the plurality of reactors. All of the reactors use the same oxygen transfer agent to produce at least one olefin. In some embodiments, at least one reactor is optimized to oxidatively couple methane to produce ethylene, while other reactors are optimized to oxidatively dehydrogenate ethane to ethylene or to oxidatively dehydrogenate propane to ethylene and/or propylene. All of the reactors feed into a single regeneration unit for the oxygen transfer agent. A method of oxidatively converting the mixed hydrocarbon feed to an olefin is also provided.

40 Claims, 5 Drawing Sheets

(51) Int. Cl.
*C07C 4/02* (2006.01)
*C07C 11/04* (2006.01)
*B01J 8/00* (2006.01)
*B01J 38/30* (2006.01)

(52) U.S. Cl.
CPC ..... *C07C 11/04* (2013.01); *B01J 2208/00805* (2013.01); *C07C 2523/78* (2013.01); *C07C 2523/84* (2013.01)

(58) Field of Classification Search
CPC ............ C07C 2521/10; C07C 2523/02; C07C 2523/04; C07C 9/06; C07C 2523/10; C07C 2523/24; C07C 2523/30; C07C 2523/34; C07C 2523/83; C07C 2523/835; C07C 2523/84; C07C 2527/14; C07C 2527/188; B01J 23/10; B01J 23/94; B01J 35/0006; B01J 23/34; B01J 23/83; B01J 23/835; B01J 23/8892; B01J 23/92; B01J 27/187; B01J 35/0013; B01J 38/04; B01J 38/12

See application file for complete search history.

(56) References Cited

U.S. PATENT DOCUMENTS

| | | | |
|---|---|---|---|
| 4,544,755 | A | 10/1985 | Withers et al. |
| 4,547,607 | A | 10/1985 | Jones et al. |
| 4,599,477 | A | 7/1986 | Robinson et al. |
| 4,670,619 | A | 6/1987 | Withers, Jr. et al. |
| 4,777,313 | A | 10/1988 | Sofranko et al. |
| 4,830,728 | A | 5/1989 | Herbst et al. |
| 5,026,947 | A | 6/1991 | Mazurek |
| 5,079,385 | A | 1/1992 | Wu |
| 5,091,163 | A | 2/1992 | Gaffney et al. |
| 5,192,809 | A | 3/1993 | Jones et al. |
| 5,545,787 | A | 8/1996 | Cooper et al. |
| 6,403,523 | B1* | 6/2002 | Cantrell ................. B01J 27/232 502/174 |
| 9,963,407 | B2* | 5/2018 | Stine ......................... C07C 5/48 |
| 10,138,182 | B2* | 11/2018 | Sofranko ................. B01J 38/12 |
| 10,550,051 | B2 | 2/2020 | Li et al. |
| 2003/0181325 | A1 | 9/2003 | Ou et al. |
| 2005/0124841 | A1 | 6/2005 | Rapier et al. |
| 2011/0245571 | A1 | 10/2011 | Kustov et al. |
| 2012/0041246 | A1 | 2/2012 | Scher et al. |
| 2012/0203042 | A1 | 8/2012 | Huber et al. |
| 2014/0275667 | A1 | 9/2014 | Sarker |
| 2014/0371504 | A1 | 12/2014 | Stine et al. |
| 2016/0122264 | A1 | 5/2016 | Olbert et al. |
| 2017/0226030 | A1 | 8/2017 | Li et al. |
| 2019/0022626 | A1 | 1/2019 | Schammel et al. |
| 2019/0315667 | A1 | 10/2019 | Sofranko et al. |
| 2020/0215515 | A1 | 7/2020 | Li et al. |

FOREIGN PATENT DOCUMENTS

| | | | |
|---|---|---|---|
| WO | 2014202501 | A1 | 12/2014 |
| WO | 2016049144 | A1 | 3/2016 |
| WO | 2018005456 | A1 | 1/2018 |
| WO | 2018049389 | A1 | 3/2018 |
| WO | 2018157042 | A1 | 8/2018 |
| WO | 2018232133 | A1 | 12/2018 |

OTHER PUBLICATIONS

Anene et al., "Experimental Study of Thermal and Catalytic Pyrolysis of Plastic Waste Components", Sustainability, 2018, 10, 3979; 11 pages.
Carey, J., "On the Brink of a Recycling Revolution?", PNAS, Jan. 24, 2017, vol. 114, No. 4, pp. 612-616.
Currao et al., "Understanding Zeolite Frameworks", Department of Chemistry and Biochemistry, University of Bern, 65 2020 pages.
Elbadawi et al., "Kinetics of oxidative cracking of n-hexane to olefins over VO2/Ce-Al2-O3 under gas phase oxygen free environment", http://onlinelibrary.wiley.com/doi/10.1002/aic.15491/ abstract, 2 pages.
Lemonick, S., "Chemistry may have solutions to our plastic trash problem", Pollution, vol. 96, Iss. 25, 2018, 9 pages.
Olazar et al, "Light olefins from HDPE cracking in a two-step thermal and catalytic process", Chemical Engineering Journal, 207-208 (2012) 27-34.
World Economic Forum, Ellen MacArthur Foundation, "The New Plastics Economy—Rethinking the Future of Plastics", http://ellenmacarthurfoundation.org/publications/the-new-plastics-economy-rethinking-the-future-of-plastics, 2014, 120 pages.
Baerlocher, "Atlas of Zeolite Framework Types," Fifth Revised Edition, 2001, 40 pages.
Baerlocher, et al., "Atlas of Zeolite Framework Types," Sixth Revised Edition, 2007, 404 pages.
Boyadjian, C. et al., Catalytic oxidative cracking of hexane as a route to olefins, 2010, Applied Catalysis A: General, vol. 372, pp. 167-174.
Breck, D.W., General Introduction, Chapter 1, Zeolite Molecular Sieves: Structure, Chemistry, and Use, Wiley, 1974, 28 pages.
Davis, B., "Identification of Molecular Sieve Structures," 1989, pp. 282-347, Van Nostrand Reinhold Catalysis Series.
Fumoto, E., et al., "Production of Light Oil by Oxidative Cracking of Oil Sand Bitumen Using Iron Oxide Catalysts in a Steam Atmosphere," Energy Fuels, 2011, pp. 524-527, vol. 25.
Garcia, J.M., et al., "The future of plastics recycling," Science, Nov. 17, 2017, vol. 358(6365), 3 pages.
Ishihara, Y., et al., "Mechanism for Gas Formation in Polyethylene Catalytic Decomposition," Polymer, 1992, vol. 33 (16), pp. 3482-3486.
Karge, et al., Post-Synthesis Modification I (Molecular Sieves), vol. 1, 2002, pp. 1-54.
Lee, H.W., et al., "Catalytic Pyrolysis of Polyethylene and Polypropylene over Desilicated Beta and A1-MSU-F," Catalysts, 2018, vol. 8(501), pp. 1-15.
Manos, G., et al., "Catalytic Degradation of High-Density polyethylene on an Ultrastable-Y Zeolite. Nature of Initial Polymer reactions, Pattern of Formation of Gas and Liquid Products, and Temperature Effects," Industrial & Engineering Chemistry Research, Mar. 25, 2000, vol. 39(5), pp. 1203-1208.
Landolt, G.R., et al., "Hydrocarbon Adsorption Characterization of Some High Silica Zeolites," pp. 547-554.
Marcilla, A., et al., "Study of the Catalytic Pyrolysis Behavior of Polyethylene-Polypropylene Mixtures," Journal of Analytical and Applied Pyrolysis, 2005, vol. 74, pp. 387-392.
Rahimi, A., et al., "Chemical Recycling of Waste Plastics for New Materials Production," Jun. 7, 2017, Nature Reviews—Chemistry, vol. 1, Article 0046, pp. 1-11.
Seo, Y-H., et al., "Investigation of Catalytic Degradation of High-Density Polyethylene by Hydrocarbon Group Type Analysis," Journal of Analytical and Applied Pyrolysis, 2003, vol. 70, pp. 383-398.
Szostak, R., Molecular Sieves—Principles of Synthesis and Identification, 17 pages, Van Nostrand Reinhold Catalysis Series.
Weitkamp, J., et al.,"Preparation of Oxide, Sulfide and Other Chalcogenide Clusters in Molecular Sieves," Molecular Sieves, 2002, vol. 3, pp. 339-414.
Xu et al., "Combination of $CH_4$ Oxidative Coupling Reaction with $C_2H_5$ Oxidative Dehydrogenation by $CO_2$ to $C_2H_4$,", Fuel, 2002, vol. 81, pp. 1593-1597.
Non Final Office Action for U.S. Appl. No. 16/845,815, dated Jun. 17, 2020, 15 pages.
Non Final Office Action for U.S. Appl. No. 16/800,883, dated Jun. 15, 2020, 30 pages.
Jordi Labs, "Typical Molecular Weights of Common Polymers", 2020 downloaded from https://jordilabs.com/blog/typical-polymer-molecular-weights, 5 pages.
Bovin et al., Electron Microscopy of Oxyborates. I. Defect Structure in the Minerals Pinakiolite, Ludwigite, Orthopinakiolite and Takéuchiite, Acta Cryst., 1981, vol. A37, pp. 28-35.
Kasper et al., "A New Structure Type for Metallic Oxides of Formula A61308", J. Chem. Phys., 1953, vol. 21, pp. 1897-1898.

(56) References Cited

OTHER PUBLICATIONS

Sofronova et al., "Ludwigites: From Natural Mineral to Modern Solid Solutions", Cryst. Res. Technol, 2017, vol. 52, No. 4, 19 pages.

De Vries et al., "The Thermal Decomposition of Potassium and Sodium-Pyrosulfate", J. Inorg. Nucl. Chem., 1968, vol. 31, pp. 1307-1313.

Neal et al., "Oxidative Dehydrogenation of Ethane: A Chemical Looping Approach", Energy Technology, 2016, vol. 4, pp. 1-10.

Sofranko et al., "The Oxidative Conversion of Methane to Higher Hydrocarbons", Journal of Catalysis, 1987, vol. 103, pp. 302-310.

Guo et al., "Recent Advances in $CaSO_4$ Oxygen Carrier for Chemical-Looping Combustion (CLC) Process", Chemical Engineering Communications, 2012, vol. 199, No. 11, pp. 1463-1491.

Non Final Office Action for U.S. Appl. No. 16/877,992, dated Aug. 7, 2020, 32 pages.

Ding, N. et al., "Effect of hematite addition to $CaSO_4$ oxygen carrier in chemical looping combustion of coal char," Jun. 15, 2015, vol. 5, pp. 56362-56376, RSC Advances, The Royal Society of Chemistry.

Li, H. et al., "Catalytic reduction of calcium sulfate to calcium sulfide by carbon monoxide," Aug. 3, 1999, vol. 38, pp. 3333-3337, Industrial & Engineering Chemistry Research.

Xiao, J. "The diffusion mechanism of hydrocarbons in zeolites," Thesis, Massachusetts Institute of Technology, Jun. 8, 1990, 195 pages.

Meng et al., "Manganese Borides Synthesized At High Pressure and High Tempreature", Journal of Applied Physics 2012, vol. 111, 6 pages.

Non Final Office Action for U.S. Appl. No. 17/110,941, dated Feb. 23, 2021, 51 pages.

\* cited by examiner

US 11,046,625 B1

REACTOR FOR OXIDATIVE CONVERSION OF HYDROCARBON FEEDS

CROSS REFERENCE TO RELATED APPLICATIONS

This application claims the benefit of and priority from U.S. Provisional Application No. 62/853,887, filed on May 29, 2019, the disclosure of which is incorporated by reference herein in its entirety for all purposes.

TECHNICAL FIELD

The present disclosure relates to a reactor and methods for oxidative coupling of methane (OCM) and the oxidative dehydrogenation (ODH) of ethane, propane and higher hydrocarbons to produce olefins.

BACKGROUND

Ethylene and propylene are important building blocks for the petrochemical industry. These olefins are used in the manufacturing of polymers such as polyethylene, polypropylene, polystyrene and many more chemicals of commercial interest. Over 90% of the global olefin production comes from the high temperature steam cracking of naphtha or ethane and propane. The steam cracking process, which utilizes furnaces, is highly energy intensive, and 1.5 to 2 tons of carbon dioxide is produced for every ton of olefin product produced.

Natural gas production from shale deposits has dramatically increased supply of methane, ethane and propane in recent years. As a result of the continued global demand for olefins and the potential for a new growing supply of ethane and propane available in natural gas liquids from shale deposits, a significant amount of interest and investment is currently centered around expanding the production capacity of ethylene and propylene derived from these new sources. Numerous olefin grass root and expansion projects are either under contract or in the planning stages to take advantage of the relative low cost liquids from wet shale gas. The supply of natural gas in the US has increased dramatically in recent years as has the co-production of shale oil. Natural gas is often produced as a mixture of methane and hydrocarbons such as ethane, propane and butanes. This so called "wet gas" often contains greater than 20% by volume of heavier components. To feed conventional ethane steam cracking furnaces, capital and energy intensive equipment is used to separate these gas components so that primarily ethane, or ethane/propane, mixtures are fed to the steam crackers. However, there are many environmental and cost challenges to bringing on this level of new capacity of steam crackers.

Olefin production is the largest emitter of $CO_2$ and NOx in the organic chemical industry. With worldwide ethylene production at ~150 MT/yr, the industry emits 150-300 MT/yr of $CO_2$ and roughly 1.4 MT/yr of NOx. Projects located in severe EPA non-attainment zones are challenged by the increase cost of NOx control. The total greenhouse gas (GHG) emission profile, reported in $CO_2$ equivalents, is another critical part of the permitting for all production expansions.

The industry continues to push for production technology that: (1) generates higher overall yield of ethylene and propylene; (2) increases the run length between furnace turnarounds (e.g. inspections, repairs, improvements, etc.); (3) lowers steam and energy utilization; (4) lowers all GHGs including carbon dioxide and NOx. ODH of ethane and propane offers a potential solution for these needs.

Oxidative dehydrogenation (ODH) provides an opportunity to improve the efficiency of olefin production. However, most current ODH processes involve highly exothermic catalytic reactions with co-fed oxygen and hydrocarbon over platinum group metal catalysts, which are expensive materials. Therefore, there is a need for improved systems and methods that promote the ODH and the analogous oxidative coupling of methane (OCM) to ethylene reaction.

SUMMARY OF THE INVENTION

The inventors have discovered that oxygen transfer agents (OTA) for promoting ODH are also useful for promoting OCM. However the optimal reaction conditions for conversion of methane to olefins are different from the optimal reaction conditions for conversion of higher hydrocarbons such as ethane or propane to olefins. Methane is generally less reactive than ethane and therefore requires either higher temperature, pressure or increased OTA/gas contact time (the reaction conditions) to obtain commercially viable conversions compare to ethane. While others have described systems that convert mixtures of methane and ethane to olefins using redox chemical looping reactors, these systems use the same reactor vessel for both methane and ethane. Therefore, optimal reaction conditions are not obtained for both feeds.

The inventors have discovered that is possible to use multiple reactors, each having different reaction conditions, but all utilizing the same OTA such that a single OTA may be used to convert a variety of hydrocarbons at different conditions, thereby obtaining the optimal conversion conditions for all feeds. Importantly, a single regeneration unit may be used to feed the multiple reactors.

In one embodiment, a system for oxidative conversion of a mixed hydrocarbon feed stream to a product stream including at least one olefin is provided. The system includes a plurality of reactors. Each reactor in the plurality of reactors is configured to receive a portion of the mixed hydrocarbon feed stream, and to receive an oxidized oxygen transfer agent. Each reactor in the plurality of reactors is also configured to oxidatively dehydrogenate, using the oxidized oxygen transfer agent, at least a portion of at least one hydrocarbon in the mixed hydrocarbon feed at one or more reactor conditions in each reactor. Thus each reactor produces a portion of the product stream including the at least one olefin and a reduced oxygen transfer agent. A regeneration unit is in communication with the plurality of reactors. The regeneration unit is configured to receive some or all of the reduced oxygen transfer agent, and to receive a gas including molecular oxygen. The regeneration unit is also configured to combine the reduced oxygen transfer agent and the gas to produce a recycled portion of the oxidized oxygen transfer agent, and to feed the recycled portion of the oxidized transfer agent to at least one reactor in the plurality of reactors.

A method for oxidative conversion of a mixed hydrocarbon feed stream to a product stream including at least one olefin is provided. The method includes the steps of: a) receiving a portion of the mixed hydrocarbon feed stream into each reactor in a plurality of reactors; b) receiving an oxidized oxygen transfer agent into each reactor in the plurality of reactors; and c) oxidatively dehydrogenating at least one hydrocarbon in the mixed hydrocarbon feed in each of the reactors at one or more reactor conditions in each reactor using the oxidized oxygen transfer agent in each of the reactors to produce a portion of the product stream including the at least one olefin and a reduced oxygen transfer agent in each of the reactors. In another embodiment, the method also includes the steps of performing the following in a regeneration unit in communication with the plurality of reactors: d) receiving some or all of the portions of the reduced oxygen transfer agent; e) receiving a gas including molecular oxygen; and f) combining the reduced oxygen transfer agent and the gas thereby producing a recycled portion of the oxidized oxygen transfer agent. The method also includes feeding the recycled portion of oxidized transfer agent to at least one reactor in the plurality of reactors.

DETAILED DESCRIPTION OF CERTAIN EMBODIMENTS

Figure 1:
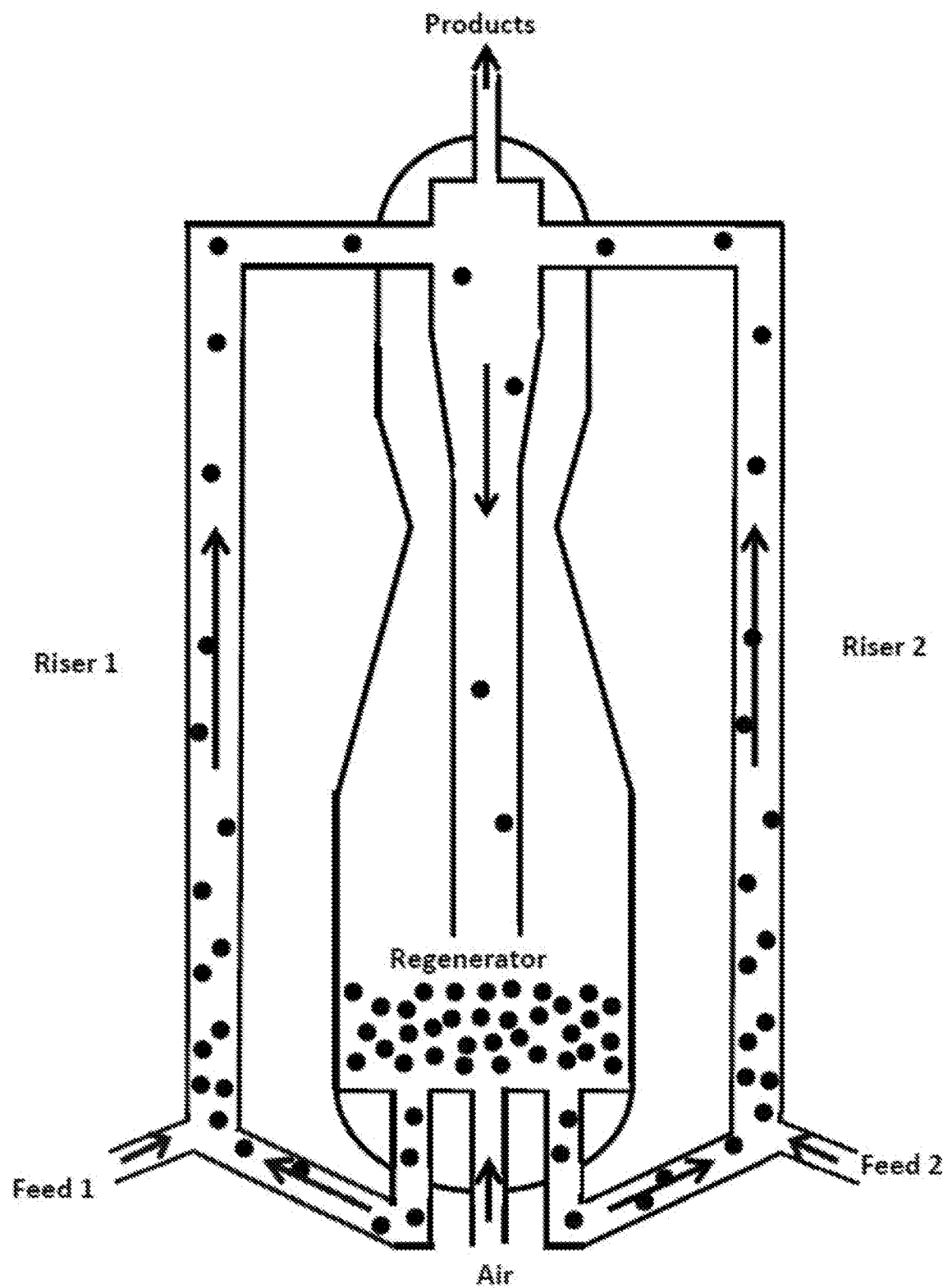
FIG. 1 shows an exemplary system according to an embodiment of the invention.

The oxidative dehydrogenation (ODH) of ethane and propane to olefins offers a production route that can significantly reduce $CO_2$ emissions and virtually eliminate NOx emissions from world scale plants. ODH is a selective process that produces primarily ethylene and water as products, and is an exothermic reaction, shown below as reaction 1.

$$CH_3CH_3 + \tfrac{1}{2}O_2 \rightarrow CH_2CH_2 + H_2O \; \Delta H° = -105 \text{ kJ/mol} \quad (1)$$

The oxidative coupling of methane (OCM) reaction to produce water is likewise exothermic, shown below as reaction 2.

$$CH_4 + \tfrac{1}{2} O_2 \rightarrow \tfrac{1}{2}CH_2CH_2 + H_2O \; \Delta H° = -175 \text{ kJ/mol} \quad (2)$$

The per-pass yields of the ODH reaction and the OCM reaction are not limited by thermodynamic equilibrium, as it is in pyrolysis. The pyrolysis of ethane is shown below as reaction 3.

$$CH_3CH_3 + \text{Heat} \leftrightarrows CH_2CH_2 + H_2 \Delta H° = +137 \text{ kJ/mol} \quad (3)$$

The oxidative coupling of methane (OCM) and the ODH of ethane and higher hydrocarbons such a propane are therefore reactions of significant commercial value. The oxidative dehydrogenation of propane, likewise is an exothermic reaction.

However, each of these reactions has different requirements for optimal reaction conditions to be efficient and selective. Accordingly, a single reactor is unlikely to achieve optimum yield of olefins from a mixed stream of hydrocarbons.

These conversions, either ODH of ethane or higher hydrocarbons or OCM may be done either catalytically by feeding a hydrocarbon and an oxygen containing gas, or in a redox oxygen transfer mode whereby an Oxygen Transfer Agent (OTA) supplies the necessary oxygen for the formation of water and the reaction proceeds without oxygen. Either system is exemplified by equation (4):

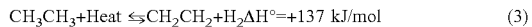
$$zCnH_{2n+2-2\beta} + (z-1+\delta)\text{"O"} \rightarrow C_{(z \times n)}H_{2(z \times n)+2-2\beta-2\delta} + (z-1+\delta)H_2O \quad (4).$$

where z=the number of reacting molecules; n=the number of atomic units in the reacting molecule; β=the degree of unsaturation where the value is zero for single bonds, one for double bonds and molecular rings, and two for triple bonds; and δ=the change in the degree of unsaturation. The oxygen, "O" in (4) may be supplied by the reduction of a metal oxide or via the catalytic use of molecular oxygen. The present inventors have found that a single OTA may be used to effect any of the reactions exemplified by reaction (4), but that differing reaction conditions are needed for each hydrocarbon (methane, ethane, propane butanes, etc.) in the feed. Either reaction (OCM or ODH) is exemplified by equation (4), and will be referred to herein as either OCM or ODH; i.e. for the purposes of this disclosure, the terms, "oxidative coupling of methane" (OCM) and "oxidative dehydrogenation" (ODH) are considered to be interchangeable.

A system for oxidative conversion of a mixed hydrocarbon feed stream to a product stream including at least one olefin is provided. The system includes a plurality of reactors and a regeneration unit in communication with the plurality of reactors. Each reactor in the plurality of reactors configured to receive a portion of the mixed hydrocarbon feed stream and an oxidized oxygen transfer agent. The oxidized oxygen transfer agent is used to oxidatively dehydrogenate at least a portion of at least one hydrocarbon in the mixed hydrocarbon feed at one or more reactor conditions in each reactor to produce a portion of the product stream including the at least one olefin and a reduced oxygen transfer agent. The regeneration unit in communication with the plurality of reactors is configured receive some or all of the reduced oxygen transfer agent, and a gas including molecular oxygen. The regeneration unit in communication with the plurality of reactors is configured to combine the reduced oxygen transfer agent and the gas to produce a recycled portion of the oxidized oxygen transfer agent, and to feed the recycled portion of the oxidized transfer agent to at least one reactor in the plurality of reactors.

According to some embodiments, the regeneration unit may be a single vessel. According to some embodiments, the regeneration unit may receive all of the reduced oxygen transfer agent.

In some embodiments, the mixed hydrocarbon stream may comprise, consist of or consist essentially of methane and ethane. The mixed hydrocarbon stream may comprise, consist of or consist essentially of, for example, any or all or a mixture of any of methane, ethane, propane, butanes, pentanes, and/or hydrocarbons having six or more carbon atoms. According to certain embodiments, the at least one olefin comprises ethylene. The at least one olefin may comprise, for example, ethylene, propylene, propadiene, butadiene, butane and isomers thereof, pentene and isomers thereof, hexene and isomers thereof. In addition, aromatic compounds may also be produced. These include but are not limited to benzene, toluene, xylenes, naphthalenes, and mixtures of any or all of these.

According to some embodiments, the mixed hydrocarbon stream may comprise, consist of or consist essentially of methane and one or more of the reactor conditions in at least one of the reactors may be optimized to oxidatively dehydrogenate and couple methane to produce at least a portion of the ethylene and one or more of the reactor conditions may be different from one or more of the reactor conditions in another of the reactors. In other embodiments, the mixed hydrocarbon stream may comprise, consist of or consist essentially of methane and ethane and one or more of the reactor conditions in at least one of the reactors may be optimized to oxidatively dehydrogenate and couple methane to produce at least a portion of the ethylene and one or more of the reactor conditions in another of the reactors may be optimized to oxidatively dehydrogenate ethane to produce at least another portion of the ethylene. In this embodiment, the one or more reactor conditions optimized to oxidatively dehydrogenate and couple methane to produce the at least a portion of the ethylene may be different from the one or more reactor conditions optimized to oxidatively dehydrogenate ethane to produce the at least another portion of the ethylene.

According to yet another embodiment of the invention, the mixed hydrocarbon stream may comprise, consist of or consist essentially of methane and propane and one or more of the reactor conditions in at least one of the reactors may be optimized to oxidatively dehydrogenate and couple methane to produce at least a portion of the ethylene and one or more of the reactor conditions in another of the reactors may be optimized to oxidatively dehydrogenate propane to produce at least another portion of the ethylene. In this embodiment, the one or more reactor conditions optimized to oxidatively dehydrogenate and couple methane to produce the at least a portion of the ethylene may be different from the one or more reactor conditions optimized to oxidatively dehydrogenate propane to produce the at least another portion of the ethylene.

In a further embodiment of the invention, the mixed hydrocarbon feed comprises methane and higher hydrocarbons and the system further comprises a separation unit coupled to at least one reactor in the plurality of reactors. The separation unit may be configured to receive at least a portion of the mixed hydrocarbon feed and to separate at least a portion of the methane from the higher hydrocarbons to produce a separated methane stream and a higher hydrocarbon stream. The separation unit may be configured to feed the separated methane stream to at least one of the reactors, and to feed the higher hydrocarbon stream to at least another of the reactors. The higher hydrocarbons may comprise, consist of or consist essentially of ethane. In an embodiment, at least one of the reactor conditions in the reactor receiving the separated methane stream is optimized to oxidatively dehydrogenate and couple methane to produce ethylene and is different from at least one of the reactor conditions in the at least another of the reactors that receives the separated higher hydrocarbon stream. In an embodiment of the invention, the higher hydrocarbons may comprise, consist of or consist essentially of ethane and at least one of the reactor conditions in the at least another of the reactors that receives the higher hydrocarbon stream may be optimized to oxidatively dehydrogenate at least a portion of the ethane to produce ethylene. In yet another embodiment, the separation unit may be further configured to separate the ethane from the mixed hydrocarbons to produce a separated ethane stream and to feed the separated ethane stream to the reactor including the reaction conditions optimized to oxidatively dehydrogenate at least a portion of the separated ethane to produce ethylene. In still another embodiment, the higher hydrocarbons may comprise, consist of or consist essentially of propane and at least one of the reactor conditions in the at least another of the reactors that receives the higher hydrocarbons may be optimized to oxidatively dehydrogenate at least a portion of the propane to produce ethylene or propylene or a mixture thereof. In a further embodiment, the separation unit may be further configured to separate the propane from the higher hydrocarbons to produce a separated propane stream and to feed the separated propane stream to the reactor including the reaction conditions optimized to oxidatively dehydrogenate at least a portion of the separated propane to produce ethylene, propylene or a mixture thereof. Further embodiments may comprise for example, a system including a separation unit or units configured to separate a stream of mixed hydrocarbons into methane, ethane and propane streams and then feeding each stream to a respective reactor having reaction conditions optimized to produce at least ethylene. Importantly, each reactor utilizes the same oxygen transfer agent and the reduced oxygen transfer agent from each reactor may to fed to the same regeneration unit.

Methods for Oxidative Conversion of a Mixed Hydrocarbon Feed Stream to a Product Stream Including at Least One Olefin A method for oxidative conversion of a mixed hydrocarbon feed stream to a product stream including at least one olefin is provided. The method comprises, consists of or consists essentially of the following steps, which are performed in each reactor in a plurality of reactors:

a) Receiving a portion of the mixed hydrocarbon feed stream into each reactor in a plurality of reactors.

b) Receiving an oxidized oxygen transfer agent into each reactor in the plurality of reactors.

c) Using the oxidized oxygen transfer agent to oxidatively dehydrogenate at least one hydrocarbon in the mixed hydrocarbon feed in each of the reactors at one or more reactor conditions in each of the reactors to produce a portion of the product stream including the at least one olefin and a reduced oxygen transfer agent in each of the reactors. The method further comprises, consists of, or consists essentially of the steps:

d) Receiving some or all of the portions of the reduced oxygen transfer agent and a gas including molecular oxygen into a regeneration unit in communication with the plurality of reactors.

e) In the regeneration unit, combining the reduced oxygen transfer agent and the gas, thereby producing a recycled portion of the oxidized oxygen transfer agent.

f) Feeding the recycled portion of oxidized transfer agent to at least one reactor in the plurality of reactors.

According to some embodiments, the regeneration unit may be a single vessel. According to some embodiments, the regeneration unit may receive all of the reduced oxygen transfer agent. In some embodiments, the mixed hydrocarbon stream may include methane and ethane. According to other embodiments of the method, the reactor conditions in at least one of the reactors may be different from one or more of the reactor conditions in another of the reactors. In an embodiment, the at least one olefin in the product stream may include ethylene. In another embodiment of the method, the mixed hydrocarbon stream may include methane and one or more of the reactor conditions in at least one of the reactors may be optimized to oxidatively dehydrogenate and couple methane to produce at least a portion of the ethylene and one or more of the reactor conditions may be different from one or more of the reactor conditions in another of the reactors. According to certain embodiments of the method, the mixed hydrocarbon stream may include methane and ethane. One or more of the reactor conditions in at least one of the reactors may be optimized to oxidatively dehydrogenate and couple methane to produce at least a portion of the ethylene. One or more of the reactor conditions in another of the reactors may be optimized to oxidatively dehydrogenate ethane to produce another portion of the ethylene. Finally, in this embodiment, one or more of the reactor conditions that may be optimized to oxidatively dehydrogenate and couple methane to produce at least a portion of the ethylene may be different from one or more of the reactor conditions optimized to oxidatively dehydrogenate ethane to produce at least another portion of the ethylene.

According to certain embodiments of the method, the mixed hydrocarbon stream may include methane and propane. According to this embodiment, one or more of the reactor conditions in at least one of the reactors may be optimized to oxidatively dehydrogenate and couple methane to produce at least a portion of the ethylene and one or more of the reactor conditions in another of the reactors may be optimized to oxidatively dehydrogenate propane to produce another portion of the ethylene. Also according to this embodiment, one or more of the reactor conditions optimized to oxidatively dehydrogenate and couple methane to produce the at least a portion of the ethylene may be different from the one or more of the reactor conditions optimized to oxidatively dehydrogenate propane to produce another portion of the ethylene or propylene or a mixture thereof.

According to still another embodiment, the method may further include a step or steps to separate the mixed hydrocarbon feed into portions. These steps may be:

a) Receiving at least a portion of the mixed hydrocarbon feed into a separation unit that is coupled to at least one reactor in the plurality of reactors.

b) Separating at least a portion of the methane from the higher hydrocarbons in the separation unit to produce a separated methane stream and a higher hydrocarbon stream.

c) Feeding, from the separation unit, the separated methane stream to at least one of the reactors.

d) Feeding, from the separation unit, the higher hydrocarbon stream to at least another of the reactors.

According to another embodiment of the method including the separation step, the reactor(s) receiving the separated methane stream may be optimized to oxidatively dehydrogenate and couple methane to produce ethylene and these reaction conditions may be different from at least one of the reactor conditions in the at least another of the reactors that receives the higher hydrocarbons. According to still another embodiment of the method that utilizes the separation step, the higher hydrocarbons may include ethane and at least one of the reactor conditions in the at least another of the reactors that receives the higher hydrocarbons may be optimized to oxidatively dehydrogenate at least a portion of the ethane to produce ethylene. The separation unit may further be configured to separate the ethane from the mixed hydrocarbons to produce a separated ethane stream and to feed the separated ethane stream to the at least another of the reactors that comprises reaction conditions optimized to produce ethylene. According to another embodiment of the method that includes the separation step, the higher hydrocarbons may comprise, consist of or consist essentially of propane and at least one of the reactor conditions in the at least another of the reactors that receives the higher hydrocarbons may be optimized to oxidatively dehydrogenate at least a portion of the propane to produce ethylene or propylene or a mixture thereof. The separation unit may further be configured to separate the propane from the mixed hydrocarbons to produced a separated propane stream and to feed the separated propane stream to the at least another of the reactors that comprises reaction conditions optimized to produce ethylene, propylene, or a mixture thereof. Other variations may be readily envisaged by a person having skill in the art, such as a separation unit constructed to separate methane, ethane and propane into separate streams and feeding each of these streams in to a reactor having reaction conditions optimized for each respective feed, and thus each respective reactor producing at least ethylene and optionally producing propylene or a mixture including propylene and ethylene, for example. Importantly, each reactor utilizes the same oxygen transfer agent and the reduced oxygen transfer agent from each reactor may be fed to the same regeneration unit.

According to embodiments of the method, the oxygen transfer agent may include at least one element selected from the group consisting of Mn, Fe, Mo, Ti, V, Pr, Cu, La, Ga and mixtures thereof. The oxygen transfer agent may be selected from the group consisting of Li/Mn/B/MgO, Li/Mn/B/CaSO$_4$/MgO, Na/Pr$_6$O$_{11}$, and mixtures thereof. According to an embodiment of the method, the oxygen transfer agent may further include at least one promotor selected from the group consisting of alkaline metals, alkaline earth metals, boron, sulfur, salts of tungstic acid, salts of halides, and mixtures thereof.

Reactors:

The reactors employed in embodiments of the system or method disclosed herein could be any system known to transport a solid particle between a reactor and a regenerator zone. Such transport systems are generally known to one of ordinary skill in the art. While not intending to be limited by these examples, useful reactors are circulating fluid beds such as fluid catalyzed cracking units, fluidized bed reactors, moving bed reactors, either co-current or counter current flow and bubbling bed reactors with means of transport of solids between the beds, or any circulating system as known in the art.

FIG. 1 shows one example of the system of present invention. In this example, Feed 1 may react in the first reactor, "Riser 1" at one set of reaction conditions and Feed 2 may react in the second reactor, "Riser 2" at another set of reaction conditions. Feed 1 and Feed 2 may have the same composition or may have different compositions, but importantly both reactors, "Riser 1" and "Riser 2," use the same oxygen transfer agent (OTA). In both cases, an oxidized OTA is fed to Riser 1 and Riser 2. The oxidized OTA provides oxygen to Feed 1 and Feed 2, respectively, to produce an olefin, water and a reduced OTA. The reduced OTA from Riser 1 and Riser 2 are combined into a regeneration unit whereby an oxidant, such as air, regenerates the OTA to its oxidized form. This oxidized OTA is then fed back to the risers or reactors. This configuration of using multiple risers, i.e. multiple reactors and one regenerator is more cost effective than building multiple reactors/risers, each with its own regeneration unit. Methods to control the appropriate circulation rate to each riser of the figure can be done independently and is generally known by those skilled in the art of reactors, particularly fluidized and moving bed reactor designs. While FIG. 1 exemplifies a two feed two reactor system, more reactors, for example up to ten or even more, each with differing reaction conditions, could be employed in certain embodiments, for up to at least ten or more different feed components.

Figure 2:
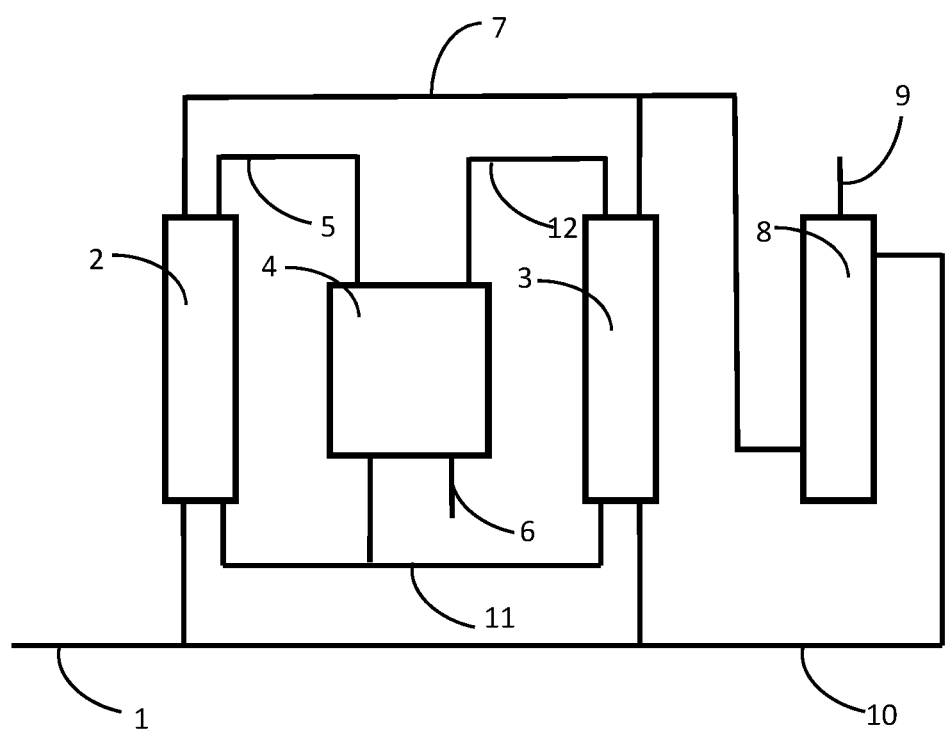
FIG. 2 shows another exemplary system according to an embodiment of the invention.

FIG. 2 illustrates another exemplary embodiment of the invention. A mixed hydrocarbon 1 is fed to reactors 2 and 3 each operating at conditions optimal for different components of the feed. For example, reactor 2 may be operating at conditions optimal for converting methane to ethylene and reactor 3 may be operating at conditions optimal for converting ethane to ethylene. If beneficial to the overall process, more reactors could be added in parallel to reactors 2 and 3. An oxidized OTA from a regenerator 4 is fed to reactors 2 and 3, via stream 11. In reactors 2 and 3 the oxidized OTA is reduced and the feed is oxidatively dehydrogenated. The reduced OTA is fed via streams 5 and 12, respectively, from 2 and 3, to the regenerator 4 where the reduced OTA reacts with an oxygen containing gas 6 to re-oxidize the OTA. The oxidized OTA 11 is fed back to the reactors 2 and 3 as noted previously. The products of oxidative dehydrogenation 7 (which may comprise ethylene, for example) are then separated in a separation unit 8 and the desired end products, for example ethylene are removed via stream 9. Unreacted hydrocarbons 10 may be recycled to the reactors 2 and 3.

Figure 3:
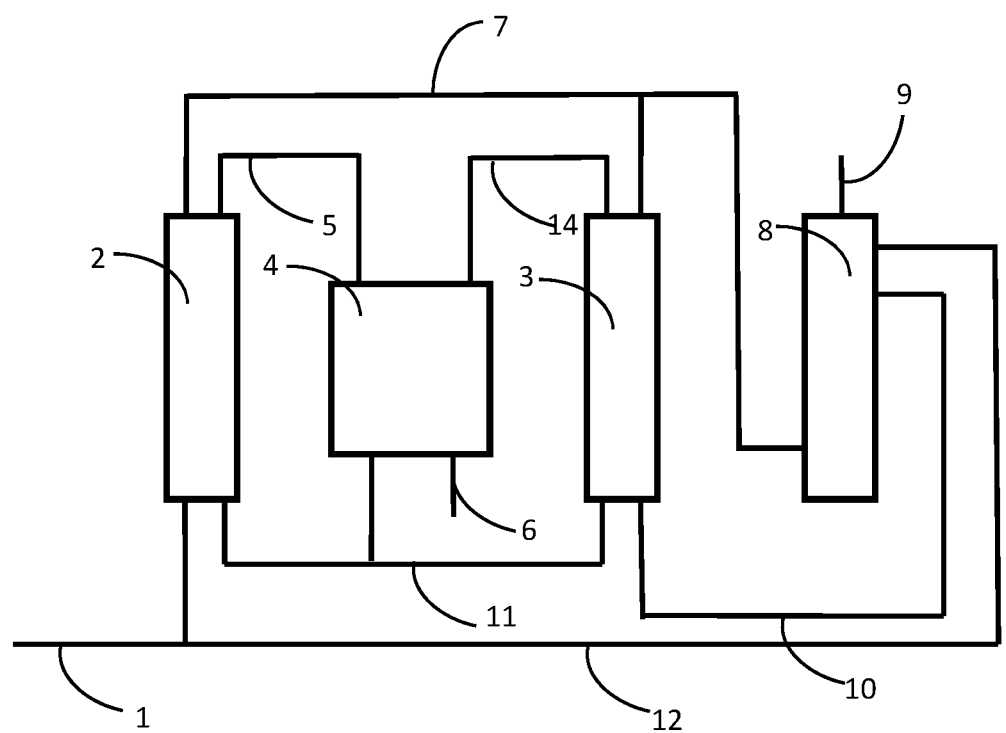
FIG. 3 shows a third embodiment of an exemplary system according to the invention.

FIG. 3 illustrates another embodiment of the invention. In this exemplary embodiment, a mixed hydrocarbon 1 is fed to reactors 2 and 3 each operating at conditions optimal for different components of the feed. If beneficial to the process, more reactors could be added in parallel to 2 and 3. An oxidized OTA from a regeneration unit 4 is added to 2 and 3 via stream 11. In the reactors 2 and 3, the OTA is reduced and the feed 1 is oxidatively dehydrogenated to produce product stream 7 and reduced oxygen transfer agent streams 5 and 14, respectively. The reduced OTA 5 and 14 from 2 and 3, or additional reactors, is fed to the regenerator 4 where it reacts with an oxygen containing gas 6 to re-oxidize the OTA to form oxidized OTA in stream 11. The oxidized OTA 11 is fed back to the reactors 2 and 3. The products of oxidative dehydrogenation 7, e.g. olefins, are then separated in a product separation unit 8 and the desired end products removed via stream 9. Separated unreacted hydrocarbons may be recycled to the reactors via streams 10 and 12.

Figure 4:
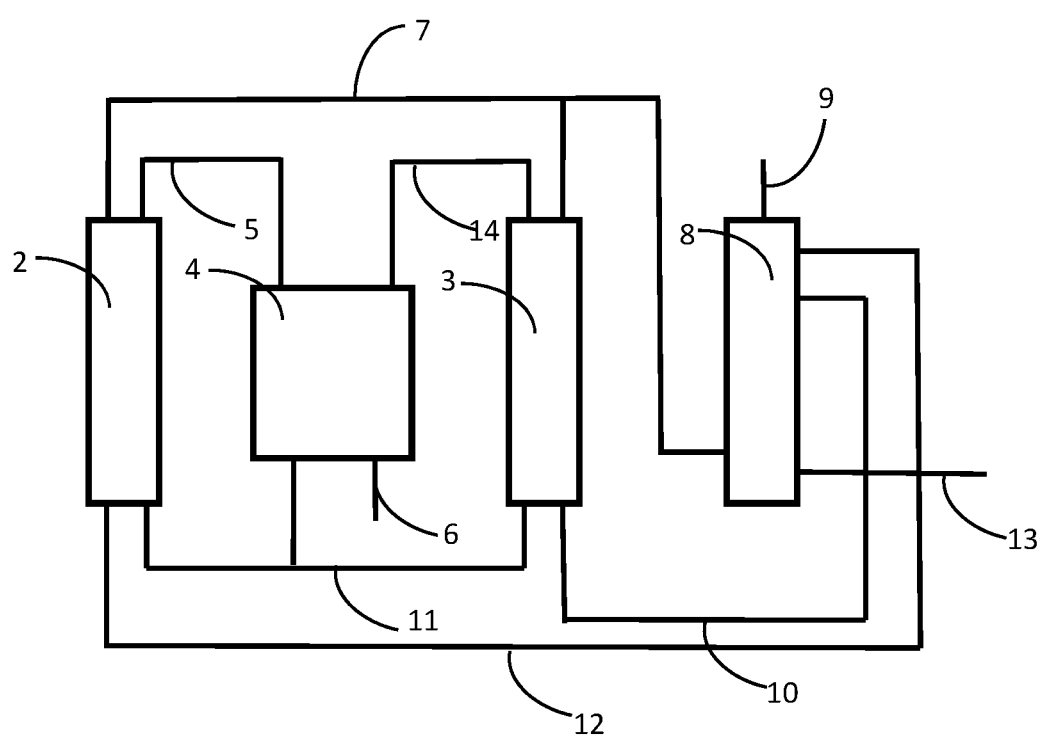
FIG. 4 shows a fourth embodiment of an exemplary system according to the invention.

FIG. 4 illustrates another embodiment of the invention. In this embodiment, a mixed hydrocarbon feed stream 13 is separated in separator 8 and the separated components 12 and 10 are fed to reactors 2 and 3, respectively. Reactors 2 and 3 are each operating at conditions optimal for components 12 and 10, respectively. These optimal conditions in each reactor 2 and 3 may be different. If beneficial to the overall process, more reactors and feed streams could be added in parallel to reactors 2 and 3. An oxidized OTA from a regeneration unit 4 is added to reactors 2 and 3 where the OTA is reduced to produce a reduced OTA and the feed to each reactor (12 and 10) is oxidatively dehydrogenated to produce product stream 7, which comprises at least some olefin. The reduced OTA in stream 5 and 14 from reactors 2 and 3, respectively, or additional reactors, is fed to the regenerator 4 where it reacts with an oxygen containing gas 6 to re-oxidize the OTA to form oxidized OTA in stream 11. The oxidized OTA 11 is fed back to the reactors 2 and 3. The products of oxidative dehydrogenation 7 are then fed to the separation unit 8 and separated into desired end products 9 and unreacted hydrocarbons 10 and 12. The desired end products, e.g. olefins are removed via product stream 9. Unreacted hydrocarbons may be recycled to the reactors 3 and 2 via 10 and 12.

Figure 5:
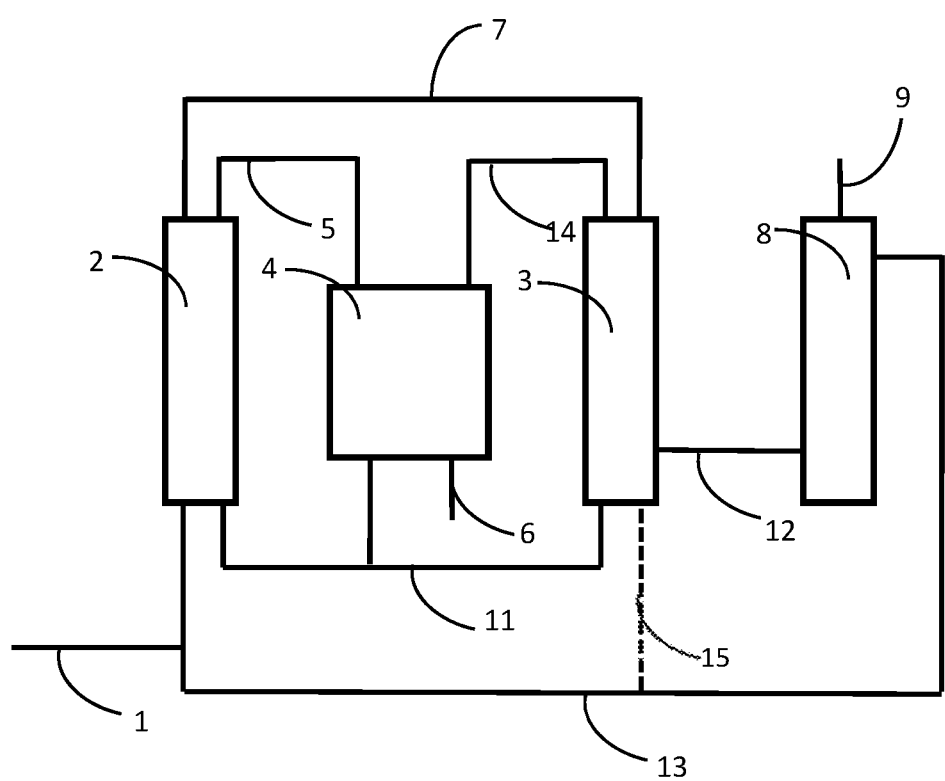
FIG. 5 shows a fifth exemplary embodiment of a system according to the invention.

FIG. 5 illustrates another exemplary embodiment of the invention. A mixed hydrocarbon feed stream 1 is fed to reactor 2 under conditions optimal to convert a portion of at least one hydrocarbon (e.g., methane) in the mixed hydrocarbon feed 1 to at least one olefin and then the product 7 (containing unreacted hydrocarbons from feed 1 and the at least one olefin) from reactor 2 is fed to reactor 3 operating at conditions optimal to convert a portion of at least one of the other hydrocarbons (e.g., ethane) in feed 1 to an olefin. The conditions optimal to convert the other hydrocarbons in reactor 3 may be different from the conditions in reactor 2 optimal to convert the portion of the at least one hydrocarbon mixed feed 1. If beneficial to the process, more reactors could be added in parallel to reactors 2 and 3. An oxidized OTA from a regeneration unit 4 is fed to reactors 2 and 3 via stream 11. In each of reactors 2 and 3, the oxidized OTA is reduced to form a reduced OTA and the feed to each reactor (stream 1 to reactor 2 and stream 7 to reactor 3) is oxidatively dehydrogenated to at least one product olefin. The reduced OTA in streams 5 and 14 from reactors 2 and 3, or additional reactors, is fed to the regenerator 4 where it reacts with an oxygen containing gas 6 to re-oxidize the OTA to form an oxidized OTA. The oxidized OTA 11 is fed back to the reactors 2 and 3 via stream 11. The products of oxidative dehydrogenation from reactor 3 are fed 12 to separation unit 8 via stream 12 and are then separated in 8 into the desired product olefins 9 and unreacted hydrocarbons 13. The desired end products (olefins) are removed via 9. Unreacted hydrocarbons stream 13 may be recycled to reactors 2 and/or 3—the dotted line stream 15 indicates an optional feed from stream 13 to reactor 3. The configuration of FIG. 5 is particularly beneficial because the reactors act to separate the mixed hydrocarbons due to the difference in reactivity of the components of the mixed hydrocarbon feed, thereby reducing the amount of separation required in the separation unit 8.

In addition, any combinations of these embodiments may be employed.

Regeneration Units:

Suitable regeneration units utilized in the system or method disclosed herein to re-oxidize the reduced oxygen transfer agent may be any of those types as known and used in the art to regenerate solid particulates, especially, but not limited to those that are suitable for contacting a particulate solid with a gas. For example, fluidized beds, rotating moving beds, recirculating fluidized beds, moving beds, either co-current or counter current flow and bubbling beds with means of transport of solids between the beds, or any circulating system as known in the art may be used to regenerate the oxygen transfer agent.

Reaction Conditions:

According to some embodiments of the system and method, one or more of the reactor conditions to effect the oxidative conversion in at least one of the reactors may be different from one or more of the reactor conditions in another of the reactors.

According to some embodiments, the reaction conditions may include the presence of essentially no molecular oxygen during the oxidative dehydrogenation of the hydrocarbon feed. In this embodiment, at least a portion of the oxygen transfer agent may be reduced to produce a reduced oxygen transfer agent. Without wishing to be bound by theory, this condition means that the oxygen needed for the oxidative dehydrogenation may be supplied by the at least one oxygen transfer agent. In particular, less than 5 wt %, less than 4 wt %, less than 3 wt %, less than 2 wt %, less than 1 wt %, less than 0.5 wt %, less than 1000 ppm weight, less than 500 ppm weight of molecular oxygen with respect to the total amount of the hydrocarbon feed, the oxygen transfer agent and the molecular oxygen is present during the oxidative dehydrogenation step. Less than 1000 ppm weight of molecular oxygen is preferred. Non-limiting examples of sources of molecular oxygen are air, or molecular oxygen-containing streams resulting from other chemical processes.

According to some embodiments the reaction conditions in step b) may include temperatures of from 825-840° C. and gas hourly space velocities of 2,400 to 4,800 hr¹. Other suitable temperatures may be from 300° C. to 1000° C., 350° C. to 1000° C., 400° C. to 1000° C., 400° C. to 800° C., or from 500° C. to 700° C. Pressure may be from subatmospheric to super-atmospheric with a range of 0.1 to 100 atm. In other embodiments, the pressure range may be 0.9 to 10 atm. Other pressure ranges may be from 0.9 to 1.5, 0.5 to 2, 0.9 to 5, 0.9 to 7, or 0.9 to 1.1 atm. 600-950° C., or from 500-900° C. or from 700-900° C. or from 800-850° C.

According to other embodiments, the reaction conditions may include providing a source of molecular oxygen in an amount of greater than 1000 ppm weight of molecular oxygen during the oxidative dehydrogenation of the hydrocarbon feed. Without wishing to be bound by theory, this condition means that the oxygen needed for the oxidative dehydrogenation of the hydrocarbon feed is supplied by the source of molecular oxygen. Accordingly, again without being bound by theory, the at least one oxygen transfer agent may be acting as a catalyst in the reaction, i.e., facilitating the oxidative dehydrogenation of the hydrocarbon feed by the source of molecular oxygen, rather than supplying the oxygen itself. According to some embodiments, more than 1000 pp weight, 2000 ppm weight, 3000 ppm weight, 0.5 wt %, more than 1 wt %, more than 5 wt %, more than 10 wt %, more than 20 wt % of molecular oxygen with respect to the total amount of the hydrocarbon feed, the oxygen transfer agent and the molecular oxygen may be supplied to the oxidative dehydrogenation step. According to some embodiments, in addition to providing the source of molecular oxygen, the reaction conditions may further include that the oxygen transfer agent include less than 5 wt %, or less than 4 wt % or less than 3 wt % or less than 2 wt % or less than 1%, or none, of a perovskite, by weight of the oxygen transfer agent. In embodiments where a source of oxygen is present during the oxidative dehydrogenation step, the oxygen transfer agent may have a form that has an aspect ratio of less than 10, or less than 9, or less than 8, or less than 7, or less than 6, or less than 5, or less than 5, or less than 4, or less than 3, or less than 2.

While in some cases it might be desirable to separate the feed components before introduction to the reactor vessel, it may also be beneficial not to separate some of the hydrocarbons and allow the reactor conditions to effect separation. In this instance of the present inventive system or method, as an example, methane and ethane could be fed to one reactor zone where ethane primarily reacts at one set of reactor conditions to form olefin products and then separation occurs between the unreacted methane and olefins formed from ODH.

In another embodiment of the present system or method, the multiple reactors may be used to selectively feed various reaction promoters with certain hydrocarbons and not with others. For example, hydrogen sulfide, oxides of sulfur or other sulfur containing gases to may be fed to one or more of the reactors to promote either OCM or ODH, and take advantage of the multiple reactors to select which feed, and to what amount, a promoter is added. According to certain embodiments of the system or method, the feature of multiple reactors utilizing a single regeneration unit may also be used to select which feed might benefit from addition of stoichiometric amounts of an oxygen containing gas to one feed to a reactor in order to accelerate the rate of conversion or flow of that feed but in another reactor or reactors, a reaction condition could be to not to have an oxygen containing gas or to minimize the presence of oxygen in the reactor in the presence of other hydrocarbon feeds.

Reactions:

According to some embodiments of the disclosed method or system, oxidatively dehydrogenating the hydrocarbon feed may proceed according to the reaction:

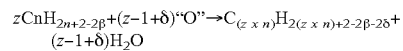

$$zCnH_{2n+2-2\beta} + (z-1+\delta)\text{"O"} \rightarrow C_{(z \times n)}H_{2(z \times n)+2-2\beta-2\delta} + (z-1+\delta)H_2O$$

wherein: z=the number of reactant molecules; n=the number of atomic units in the reactant molecule; β=the degree of unsaturation in the reactant molecule, where the value is zero for single bonds, and one for double bonds and molecular rings; δ=the change in the degree of unsaturation from the reactant molecule to the product molecule; and "O" is atomic oxygen; and wherein the atomic oxygen is supplied by the at least one oxygen transfer agent. According to some embodiments, z=2, n=1, β=0, and δ=0. In particular this means that the reaction may include the oxidative coupling of methane to form ethylene. According to other embodiments, z=1, n=2, β=0, and δ=1. In particular, this means that the reaction may include the oxidative dehydrogenation of ethane to form ethylene. The oxidative dehydrogenation may include more than one reaction. Non-limiting examples of such multiple reactions may include: skeletal isomerization of olefins; oxidative dehydrogenation of methane to ethane and ethylene, and oxidative dehydrogenation of ethane to ethylene and higher olefins such as propylene and butylene.

Hydrocarbon Feed:

Suitable mixed hydrocarbon feeds for use in embodiments of the present system or method invention may be selected from methane; ethane; propane; isomers of butane; isomers of butene, isomers of pentane; isomers of pentene; isomers of hexane; cyclohexane; isomers of hexene; cyclohexene; naphtha; gas oil; and mixtures thereof. As used here, the term "mixed hydrocarbon feed" means a feed including two or more different hydrocarbons, for example a feed stream containing methane and ethane.

Oxygen Transfer Agents:

Non-limiting examples of suitable oxygen transfer agents for use in embodiments of the present invention may include at least one element selected from the group consisting of Mn, Fe, Mo, Ti, V, Pr, Cu, La, Ga and mixtures thereof. A suitable oxygen transfer agent may include Li/Mn/B/MgO, Li/Mn/B/CaSO$_4$/MgO, Na/Pr$_6$O$_{11}$, and mixtures thereof. In an embodiment, the oxygen transfer agent may further include at least one promotor selected from the group consisting of alkaline metals, alkaline earth metals, boron, sulfur, salts of tungstic acid, salts of halides, and mixtures thereof. Other suitable oxygen transfer agents that may be used in embodiments of this invention are those that are described in copending United States patent application U.S. Ser. No. 16/800,883 filed on Feb. 25, 2020; U.S. Ser. No. 16/845,815 filed on Apr. 10, 2020; and U.S. Ser. No. 16/877,992 filed May 20, 2020, the contents of each of which are incorporated by reference herein in their entireties for all purposes.

Aspects of the invention may be summarized as follows:

Aspect 1: A system for oxidative conversion of a mixed hydrocarbon feed stream to a product stream comprising at least one olefin, the system comprising:

a plurality of reactors, each reactor in the plurality of reactors configured to:

receive a portion of the mixed hydrocarbon feed stream, receive an oxidized oxygen transfer agent, oxidatively dehydrogenate at least a portion of at least one hydrocarbon in the mixed hydrocarbon feed stream at one or more reactor conditions in each reactor using the oxidized oxygen transfer agent to produce a portion of the product stream comprising the at least one olefin and a reduced oxygen transfer agent; and a regeneration unit in communication with at least one of the plurality of reactors and configured to:
receive some or all of the reduced oxygen transfer agent,
receive a gas comprising molecular oxygen,
combine the reduced oxygen transfer agent and the gas to produce a recycled portion of the oxidized oxygen transfer agent, and
feed the recycled portion of the oxidized transfer agent to at least one reactor in the plurality of reactors.

Aspect 2: The system of Aspect 1, wherein the regeneration unit is a single vessel.

Aspect 3: The system of Aspect 1 or Aspect 2, wherein the regeneration unit is in communication with all of the reactors in the plurality of reactors.

Aspect 4: The system of any of Aspects 1-3, wherein the regeneration unit receives all of the reduced oxygen transfer agent.

Aspect 5: The system of any of Aspects 1-4, wherein the mixed hydrocarbon feed stream comprises methane and ethane.

Aspect 6: The system of any of Aspects 1-5, wherein one or more of the reactor conditions in at least one of the reactors is different from one or more of the reactor conditions in another of the reactors.

Aspect 7: The system of any of Aspects 1-6, wherein the at least one olefin comprises ethylene.

Aspect 8: The system of Aspect 7, wherein the mixed hydrocarbon feed stream comprises methane and one or more of the reactor conditions in at least one of the reactors is optimized to oxidatively dehydrogenate and couple methane to produce at least a portion of the ethylene and one or more of the reactor conditions is different from one or more of the reactor conditions in another of the reactors.

Aspect 9: The system of Aspect 7 or Aspect 8, wherein the mixed hydrocarbon feed stream comprises methane and ethane and one or more of the reactor conditions in at least one of the reactors is optimized to oxidatively dehydrogenate and couple methane to produce at least a portion of the ethylene and one or more of the reactor conditions in another of the reactors is optimized to oxidatively dehydrogenate ethane to produce at least another portion of the ethylene, and the one or more reactor conditions optimized to oxidatively dehydrogenate and couple methane to produce the at least a portion of the ethylene is different from the one or more reactor conditions optimized to oxidatively dehydrogenate ethane to produce the at least another portion of the ethylene.

Aspect 10: The system of any of Aspects 7-9, wherein the mixed hydrocarbon feed stream comprises methane and propane and one or more of the reactor conditions in at least one of the reactors is optimized to oxidatively dehydrogenate and couple methane to produce at least a portion of the ethylene and one or more of the reactor conditions in another of the reactors is optimized to oxidatively dehydrogenate propane to produce at least another portion of the ethylene, and the one or more reactor conditions optimized to oxidatively dehydrogenate and couple methane to produce the at least a portion of the ethylene is different from the one or more reactor conditions optimized to oxidatively dehydrogenate propane to produce the at least another portion of the ethylene.

Aspect 11: The system of any of Aspects 1-10, wherein the mixed hydrocarbon feed stream comprises methane and higher hydrocarbons and the system further comprises a separation unit coupled to at least one reactor in the plurality of reactors and is configured to:
receive at least a portion of the mixed hydrocarbon feed,
separate at least a portion of the methane from the mixed hydrocarbon feed stream to produce a methane stream and a higher hydrocarbon stream,
feed the separated methane stream to at least one of the reactors, and
feed the higher hydrocarbon stream to at least another of the reactors.

Aspect 12. The system of Aspect 11, wherein at least one of the reactor conditions in the reactor receiving the separated methane stream is optimized to oxidatively dehydrogenate and couple methane to produce ethylene and is different from at least one of the reactor conditions in the at least another of the reactors that receives the higher hydrocarbon stream.

Aspect 13: The system of Aspect 11 or Aspect 12, wherein the higher hydrocarbon stream comprises ethane and at least one of the reactor conditions in the at least another of the reactors that receives the higher hydrocarbon stream is optimized to oxidatively dehydrogenate at least a portion of the ethane to produce ethylene.

Aspect 14: The system of Aspect 13, wherein the separation unit is further configured to separate at least a portion of the ethane from the mixed hydrocarbon feed stream to produce a separated ethane stream and to feed the separated ethane stream to the at least another of the reactors that is optimized to oxidatively dehydrogenate at least a portion of the ethane to produce ethylene.

Aspect 15: The system of any of Aspects 12-14, wherein the higher hydrocarbons comprise propane and at least one of the reactor conditions in the at least another of the reactors that receives the higher hydrocarbons is optimized to oxidatively dehydrogenate at least a portion of the propane to produce ethylene, or propylene, or a mixture thereof.

Aspect 16: The system of Aspect 15, wherein the separation unit is further configured to separate at least a portion of the propane from the mixed hydrocarbon feed stream to produce a separated propane stream and to feed the separated propane stream to the at least another of the reactors that is optimized to oxidatively dehydrogenate at least a portion of the propane to produce ethylene, propylene, or a mixture thereof.

Aspect 17: The system of any of Aspects 1-16 wherein the oxygen transfer agent comprises at least one element selected from the group consisting of Mn, Fe, Mo, Ti, V, Pr, Cu, La, Ga and mixtures thereof.

Aspect 18: The system of Aspect 17, wherein the oxygen transfer agent further comprises at least one promotor selected from the group consisting of alkaline metals, alkaline earth metals, boron, sulfur, salts of tungstic acid, salts of halides, and mixtures thereof.

Aspect 19: The system of any of Aspects 1-18, wherein the oxygen transfer agent is selected from the group consisting of Li/Mn/B/MgO, Li/Mn/B/CaSO$_4$/MgO, Na/Pr$_6$O$_{11}$, and mixtures thereof.

Aspect 20: A method for oxidative conversion of a mixed hydrocarbon feed stream to a product stream comprising at least one olefin, the method comprising:
receiving a portion of the mixed hydrocarbon feed stream into each reactor in a plurality of reactors,
receiving an oxidized oxygen transfer agent into each reactor in the plurality of reactors,
oxidatively dehydrogenating at least one hydrocarbon in the mixed hydrocarbon feed stream in each of the reactors at one or more reactor conditions in each reactor using the oxidized oxygen transfer agent in each of the reactors to produce a portion of the product stream comprising the at least one olefin and a reduced oxygen transfer agent in each of the reactors; and in a regeneration unit in communication with at least one reactor in the plurality of reactors:

receiving some or all of the portions of the reduced oxygen transfer agent, receiving a gas comprising molecular oxygen, combining the reduced oxygen transfer agent and the gas thereby producing a recycled portion of the oxidized oxygen transfer agent, and feeding the recycled portion of oxidized transfer agent to at least one reactor in the plurality of reactors.

Aspect 21: The method of Aspect 20, wherein the regeneration unit is a single vessel.

Aspect 22: The method of either Aspect 20 or Aspect 21, wherein the regeneration unit is in communication with each of the reactors in the plurality of reactors.

Aspect 23: The method of any of Aspects 20-22, wherein the regeneration unit receives all of the reduced oxygen transfer agent.

Aspect 24: The method of any of Aspects 20-23, wherein the mixed hydrocarbon feed stream comprises methane and ethane.

Aspect 25: The method of any of Aspects 20-24, wherein one or more of the reactor conditions in at least one of the reactors is different from one or more of the reactor conditions in another of the reactors.

Aspect 26: The method of any of Aspects 20-25, wherein the at least one olefin comprises ethylene.

Aspect 27: The method of Aspect 26, wherein the mixed hydrocarbon feed stream comprises methane and one or more of the reactor conditions in at least one of the reactors is optimized to oxidatively dehydrogenate and couple methane to produce at least a portion of the ethylene and one or more of the reactor conditions is different from one or more of the reactor conditions in another of the reactors.

Aspect 28: The method of Aspect 26 or Aspect 27, wherein the mixed hydrocarbon feed stream comprises methane and ethane and one or more of the reactor conditions in at least one of the reactors is optimized to oxidatively dehydrogenate and couple methane to produce at least a portion of the ethylene and one or more of the reactor conditions in another of the reactors is optimized to oxidatively dehydrogenate ethane to produce another portion of the ethylene, and one or more of the reactor conditions optimized to oxidatively dehydrogenate and couple methane to produce the at least a portion of the ethylene is different from one or more of the reactor conditions optimized to oxidatively dehydrogenate ethane to produce the at least another portion of the ethylene.

Aspect 29: The method of any of Aspects 26-28, wherein the mixed hydrocarbon feed stream comprises methane and propane and one or more of the reactor conditions in at least one of the reactors is optimized to oxidatively dehydrogenate and couple methane to produce at least a portion of the ethylene and one or more of the reactor conditions in another of the reactors is optimized to oxidatively dehydrogenate propane to produce another portion of the ethylene, and one or more of the reactor conditions optimized to oxidatively dehydrogenate and couple methane to produce the at least a portion of the ethylene is different from one or more of the reactor conditions optimized to oxidatively dehydrogenate propane to produce the at least another portion of the ethylene.

Aspect 30: The method of any of Aspects 20-29, wherein the mixed hydrocarbon feed stream comprises methane and higher hydrocarbons and the method further comprises a separation step comprising:

receiving at least a portion of the mixed hydrocarbon feed into a separation unit that is coupled to at least one reactor in the plurality of reactors, separating at least a portion of the methane from the higher hydrocarbons in the separation unit to produce a separated methane stream and a higher hydrocarbon stream, feeding, from the separation unit, the separated methane stream to at least one of the reactors, and feeding, from the separation unit, the higher hydrocarbon stream to at least another of the reactors.

Aspect 31: The method of Aspect 30, wherein at least one of the reactor conditions in the reactor receiving the separated methane stream is optimized to oxidatively dehydrogenate and couple methane to produce ethylene and is different from at least one of the reactor conditions in the at least another of the reactors that receives the higher hydrocarbon stream.

Aspect 32: The method of Aspect 31, wherein the higher hydrocarbons comprise ethane and at least one of the reactor conditions in the at least another of the reactors that receives the higher hydrocarbon stream is optimized to oxidatively dehydrogenate at least a portion of the ethane to produce ethylene.

Aspect 33: The method of Aspect 32, wherein the separation unit is further configured to separate at least a portion of the ethane from the mixed hydrocarbon feed stream to produce a separated ethane stream and to feed the separated ethane stream to the at least another of the reactors that is optimized to oxidatively dehydrogenate at least a portion of the ethane to produce ethylene.

Aspect 34: The method of any of Aspects 31-33, wherein the higher hydrocarbons comprise propane and at least one of the reactor conditions in the at least another of the reactors that receives the higher hydrocarbons is optimized to oxidatively dehydrogenate at least a portion of the propane to produce ethylene, propylene, or a mixture thereof.

Aspect 35: The method of Aspect 34, wherein the separation unit is further configured to separate at least a portion of the propane from the mixed hydrocarbon feed stream to produce a separated propane stream and to feed the separated propane stream to the at least another of the reactors that is optimized to oxidatively dehydrogenate at least a portion of the propane to produce ethylene, propylene, or a mixture thereof.

Aspect 36: The method of any of Aspects 20-35 wherein the oxygen transfer agent comprises at least one element selected from the group consisting of Mn, Fe, Mo, Ti, V, Pr, Cu, La, Ga and mixtures thereof.

Aspect 37: The method of Aspect 36, wherein the oxygen transfer agent further comprises at least one promotor selected from the group consisting of alkaline metals, alkaline earth metals, boron, sulfur, salts of tungstic acid, salts of halides, and mixtures thereof.

Aspect 38: The method of any of Aspects 20-37, wherein the oxygen transfer agent is selected from the group consisting of Li/Mn/B/MgO, Li/Mn/B/CaSO$_4$/MgO, Na/Pr$_6$O$_{11}$, and mixtures thereof.

EXAMPLES

The following non-limiting examples are provided for the purpose of elucidating the advantages obtained from aspects of the present invention and are not intended to limit the invention to only these exemplary embodiments.

Example 1

An OTA was prepared by dry mixing 10 g of $MnO_2$, 12.98 g of MgO, 3.55 g of $H_3BO_3$ and 1.38 g of LiOH. Sufficient distilled water was added to the mixture in order to form a wet paste. This paste was ball milled for 3 hours, dried at 110° C. overnight and then calcined in air at 950° C. for 16 hours. The resultant hard material was broken down and sieved to 14-30 mesh. A ½ inch ID alumina tube was charged with 5 ml of OTA. OCM and ODH runs were made using methane and ethane as feeds at 500-4800 $hr^{-1}$ gas hourly space velocity (GHSV) and 825-840° C. Product was collected in a gas bag for the first 15 seconds of the run and analyzed by GC. The reactor was then purged with a nitrogen flow, oxidized by air for 10 minutes with nitrogen. This sequence was then repeated many times. Representative run results are shown in Table 1.

Example 2

An OTA was prepared by dry mixing 10 g of $MnO_2$, 12.98 g of MgO, 3.55 g of $H_3BO_3$, 1.38 g of LiOH and 9.91 g of $CaSO_4$. Sufficient distilled water was added to the mixture in order to form a wet paste. This paste was ball milled for 3 hours, dried at 110° C. overnight and then calcined in air at 950° C. for 16 hours. The resultant hard material was broken down and sieved to 14-30 mesh. A ½ inch ID alumina tube was charged with 5 ml of the OTA. OCM and ODH runs were made using methane and ethane as feeds at 500-4800 hr-1 GHSV and 825-840° C. The resulting product was collected in a gas bag for the first 15 seconds of the run and analyzed by GC. The reactor was then purged with a nitrogen flow, and then oxidized by air for 10 minutes and then purged again with nitrogen. This sequence was then repeated many times. Representative run results are shown in Table 1.

Example 3

An OTA was made by addition of sufficient sodium nitrate via incipient wetness to yield 5 weight % sodium on $Pr_6O_{11}$. After drying at 110° C., the material was calcined in air at 950 C for 12 hours. The resultant hard material was broken down and sieved to 14-30 mesh. A ½ inch ID alumina tube was charged with 5 ml of OTA. OCM and ODH runs were made using methane and ethane as feeds at 500-4800 hr-1 GHSV and 750-840° C. The resulting product was collected in a gas bag for the first 15 seconds of the run and analyzed by GC. The reactor was then purged with a nitrogen flow, and subsequently oxidized by air for 10 minutes and then purged again with nitrogen. This sequence was then repeated many times.

Representative run results for Examples 1-3 are shown in Table 1 below.

TABLE 1

OCM and ODH results using various OTAs

| | | Example | | | | | |
|---|---|---|---|---|---|---|---|
| | | 1 | | 2 | | 3 | |
| | | Oxygen Transfer Agent | | | | | |
| | | Li/Mn/B/MgO | | Li/Mn/B/CaSO4/MgO | | Na/Pr6O11 | |
| | | Feed | | | | | |
| | | Ethane | Methane | Ethane | Methane | Ethane | Methane |
| | Temp, ° C. | 840 | 825 | 840 | 825 | 750 | 750 |
| | GHSV, $hr^{-1}$ | 4800 | 1200 | 4800 | 1200 | 2400 | 1200 |
| % Selectivity | Methane/Ethane | 10.44 | 10.06 | 8.73 | 9.74 | 3.27 | 29.37 |
| | Ethylene | 71.80 | 47.43 | 70.15 | 53.71 | 68.86 | 44.01 |
| | Acetylene | 0.78 | 2.09 | 2.08 | 2.10 | 0.07 | 0.09 |
| | Propylene | 2.33 | 4.54 | 1.87 | 6.01 | 2.25 | 4.63 |
| | Propadiene | 0.42 | 0.36 | 0.04 | 0.21 | 0.01 | 0.04 |
| | Propane | 0.04 | 0.13 | 0.30 | 0.61 | 1.04 | 2.72 |
| | Methyl acetylene | 0.20 | 0.45 | 0.23 | 0.58 | 0.05 | 0.00 |
| | $C_4$ | 4.43 | 2.70 | 4.32 | 6.45 | 6.77 | 6.28 |
| | $C_5$ | 1.20 | 0.90 | 0.07 | 1.96 | 2.06 | 1.22 |
| | $C_6+$ | 3.96 | 3.42 | 9.90 | 1.63 | 2.46 | 0.27 |
| | Coke | N.D. | N.D. | N.D. | N.D. | N.D. | N.D. |
| | $CO_2$ | 2.77 | 19.08 | 1.23 | 11.92 | 13.17 | 11.37 |
| | CO | 1.64 | 8.84 | 1.09 | 5.09 | 0.00 | 0.00 |
| % Conversion of Feed | | 84.11 | 27.52 | 86.06 | 34.18 | 62.13 | 24.14 |
| % Selectivity of Olefins | | 85.15 | 72.07 | 88.95 | 82.99 | 83.56 | 88.63 |
| % Yield of Olefins | | 71.62 | 19.83 | 76.55 | 28.37 | 51.92 | 21.39 |
| % $H_2$ Selectivity | | 28.50 | 6.58 | 25.70 | 2.41 | 7.18 | 10.38 |
| % $H_2O$ Selectivity | | 71.50 | 93.42 | 74.30 | 97.59 | 92.82 | 89.62 |

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the invention. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A system for oxidative conversion of a mixed hydrocarbon feed stream to a product stream comprising at least one olefin and water, the system comprising:
a plurality of reactors, each reactor in the plurality of reactors configured to:
receive a portion of the mixed hydrocarbon feed stream,
receive an oxidized oxygen transfer agent,
oxidatively dehydrogenate at least a portion of at least one hydrocarbon in the mixed hydrocarbon feed stream at one or more reactor conditions in each reactor using the oxidized oxygen transfer agent to produce a portion of the product stream comprising the at least one olefin, the water, and a reduced oxygen transfer agent, wherein the plurality of reactors are arranged in parallel, at least one of the reactor conditions in at least one of the reactors in the plurality of reactors comprises a presence of less than 1000 ppm of molecular oxygen with respect to a weight of the portion of the mixed hydrocarbon feed stream, and the oxygen in the water is provided by a reduction of the oxidized oxygen transfer agent to produce the reduced oxygen transfer agent; and
a regeneration unit in communication with at least one of the plurality of reactors and configured to:
receive some or all of the reduced oxygen transfer agent,
receive a gas comprising molecular oxygen,
combine the reduced oxygen transfer agent and the gas to produce a recycled portion of the oxidized oxygen transfer agent, and
feed the recycled portion of the oxidized transfer agent to at least one reactor in the plurality of reactors.

2. The system of claim 1, wherein the regeneration unit is a single vessel.

3. The system of claim 1, wherein the regeneration unit is in communication with all of the reactors in the plurality of reactors.

4. The system of claim 1, wherein the regeneration unit receives all of the reduced oxygen transfer agent.

5. The system of claim 1, wherein the mixed hydrocarbon feed stream comprises methane and ethane.

6. The system of claim 1, wherein one or more of the reactor conditions in at least one of the reactors is different from one or more of the reactor conditions in another of the reactors.

7. The system of claim 1, wherein the at least one olefin comprises ethylene.

8. The system of claim 7, wherein the mixed hydrocarbon feed stream comprises methane and one or more of the reactor conditions in at least one of the reactors is optimized to oxidatively dehydrogenate and couple methane to produce at least a portion of the ethylene and one or more of the reactor conditions is different from one or more of the reactor conditions in another of the reactors.

9. The system of claim 7, wherein the mixed hydrocarbon feed stream comprises methane and ethane and one or more of the reactor conditions in at least one of the reactors is optimized to oxidatively dehydrogenate and couple methane to produce at least a portion of the ethylene and one or more of the reactor conditions in another of the reactors is optimized to oxidatively dehydrogenate ethane to produce at least another portion of the ethylene, and the one or more reactor conditions optimized to oxidatively dehydrogenate and couple methane to produce the at least a portion of the ethylene is different from the one or more reactor conditions optimized to oxidatively dehydrogenate ethane to produce the at least another portion of the ethylene.

10. The system of claim 7, wherein the mixed hydrocarbon feed stream comprises methane and propane and one or more of the reactor conditions in at least one of the reactors is optimized to oxidatively dehydrogenate and couple methane to produce at least a portion of the ethylene and one or more of the reactor conditions in another of the reactors is optimized to oxidatively dehydrogenate propane to produce at least another portion of the ethylene, and the one or more reactor conditions optimized to oxidatively dehydrogenate and couple methane to produce the at least a portion of the ethylene is different from the one or more reactor conditions optimized to oxidatively dehydrogenate propane to produce the at least another portion of the ethylene.

11. The system of claim 1, wherein the mixed hydrocarbon feed stream comprises methane and higher hydrocarbons and the system further comprises a separation unit coupled to at least one reactor in the plurality of reactors and is configured to:
receive at least a portion of the mixed hydrocarbon feed,
separate at least a portion of the methane from the mixed hydrocarbon feed stream to produce a methane stream and a higher hydrocarbon stream,
feed the separated methane stream to at least one of the reactors, and
feed the higher hydrocarbon stream to at least another of the reactors.

12. The system of claim 11, wherein at least one of the reactor conditions in the reactor receiving the separated methane stream is optimized to oxidatively dehydrogenate and couple methane to produce ethylene and is different from at least one of the reactor conditions in the at least another of the reactors that receives the higher hydrocarbon stream.

13. The system of claim 12, wherein the higher hydrocarbon stream comprises ethane and at least one of the reactor conditions in the at least another of the reactors that receives the higher hydrocarbon stream is optimized to oxidatively dehydrogenate at least a portion of the ethane to produce ethylene.

14. The system of claim 13, wherein the separation unit is further configured to separate at least a portion of the ethane from the mixed hydrocarbon feed stream to produce a separated ethane stream and to feed the separated ethane stream to the at least another of the reactors that is optimized to oxidatively dehydrogenate at least a portion of the ethane to produce ethylene.

15. The system of claim 12, wherein the higher hydrocarbons comprise propane and at least one of the reactor conditions in the at least another of the reactors that receives the higher hydrocarbons is optimized to oxidatively dehydrogenate at least a portion of the propane to produce ethylene, or propylene, or a mixture thereof.

16. The system of claim 15, wherein the separation unit is further configured to separate at least a portion of the propane from the mixed hydrocarbon feed stream to produce a separated propane stream and to feed the separated propane stream to the at least another of the reactors that is optimized to oxidatively dehydrogenate at least a portion of the propane to produce ethylene, propylene, or a mixture thereof.

17. The system of claim 1 wherein the oxygen transfer agent comprises at least one element selected from the group consisting of Mn, Fe, Mo, Ti, V, Pr, Cu, La, Ga and mixtures thereof.

18. The system of claim 17, wherein the oxygen transfer agent further comprises at least one promotor selected from the group consisting of alkaline metals, alkaline earth metals, boron, sulfur, salts of tungstic acid, salts of halides, and mixtures thereof.

19. The system of claim 1, wherein the oxygen transfer agent is selected from the group consisting of Li/Mn/B/MgO, Li/Mn/B/CaSO$_4$/MgO, Na/Pr$_6$O$_{11}$, and mixtures thereof.

20. A method for oxidative conversion of a mixed hydrocarbon feed stream to a product stream comprising at least one olefin and water, the method comprising:
    receiving a portion of the mixed hydrocarbon feed stream into each reactor in a plurality of reactors,
    receiving an oxidized oxygen transfer agent into each reactor in the plurality of reactors, oxidatively dehydrogenating at least one hydrocarbon in the mixed hydrocarbon feed stream in each of the reactors at one or more reactor conditions in each reactor using the oxidized oxygen transfer agent in each of the reactors to produce a portion of the product stream comprising the at least one olefin, the water, and a reduced oxygen transfer agent in each of the reactors, wherein the plurality of reactors are arranged in parallel, at least one of the reactor conditions in at least one of the reactors in the plurality of reactors comprises a presence of less than 1000 ppm of molecular oxygen with respect to a weight of the portion of the mixed hydrocarbon feed stream, and the oxygen in the water is provided by a reduction of the oxidized oxygen transfer agent to produce the reduced oxygen transfer agent; and
    in a regeneration unit in communication with at least one reactor in the plurality of reactors:
    receiving some or all of the portions of the reduced oxygen transfer agent,
    receiving a gas comprising molecular oxygen,
    combining the reduced oxygen transfer agent and the gas thereby producing a recycled portion of the oxidized oxygen transfer agent, and
    feeding the recycled portion of oxidized transfer agent to at least one reactor in the plurality of reactors.

21. The method of claim 20, wherein the regeneration unit is a single vessel.

22. The method of claim 20, wherein the regeneration unit is in communication with each of the reactors in the plurality of reactors.

23. The method of claim 20, wherein the regeneration unit receives all of the reduced oxygen transfer agent.

24. The method of claim 20, wherein the mixed hydrocarbon feed stream comprises methane and ethane.

25. The method of claim 20, wherein one or more of the reactor conditions in at least one of the reactors is different from one or more of the reactor conditions in another of the reactors.

26. The method of claim 20, wherein the at least one olefin comprises ethylene.

27. The method of claim 26, wherein the mixed hydrocarbon feed stream comprises methane and one or more of the reactor conditions in at least one of the reactors is optimized to oxidatively dehydrogenate and couple methane to produce at least a portion of the ethylene and one or more of the reactor conditions is different from one or more of the reactor conditions in another of the reactors.

28. The method of claim 26, wherein the mixed hydrocarbon feed stream comprises methane and ethane and one or more of the reactor conditions in at least one of the reactors is optimized to oxidatively dehydrogenate and couple methane to produce at least a portion of the ethylene and one or more of the reactor conditions in another of the reactors is optimized to oxidatively dehydrogenate ethane to produce another portion of the ethylene, and one or more of the reactor conditions optimized to oxidatively dehydrogenate and couple methane to produce the at least a portion of the ethylene is different from one or more of the reactor conditions optimized to oxidatively dehydrogenate ethane to produce the at least another portion of the ethylene.

29. The method of claim 26, wherein the mixed hydrocarbon feed stream comprises methane and propane and one or more of the reactor conditions in at least one of the reactors is optimized to oxidatively dehydrogenate and couple methane to produce at least a portion of the ethylene and one or more of the reactor conditions in another of the reactors is optimized to oxidatively dehydrogenate propane to produce another portion of the ethylene, and one or more of the reactor conditions optimized to oxidatively dehydrogenate and couple methane to produce the at least a portion of the ethylene is different from one or more of the reactor conditions optimized to oxidatively dehydrogenate propane to produce the at least another portion of the ethylene.

30. The method of claim 20, wherein the mixed hydrocarbon feed stream comprises methane and higher hydrocarbons and the method further comprises a separation step comprising:
    receiving at least a portion of the mixed hydrocarbon feed into a separation unit that is coupled to at least one reactor in the plurality of reactors,
    separating at least a portion of the methane from the higher hydrocarbons in the separation unit to produce a separated methane stream and a higher hydrocarbon stream,
    feeding, from the separation unit, the separated methane stream to at least one of the reactors, and
    feeding, from the separation unit, the higher hydrocarbon stream to at least another of the reactors.

31. The method of claim 30, wherein at least one of the reactor conditions in the reactor receiving the separated methane stream is optimized to oxidatively dehydrogenate and couple methane to produce ethylene and is different from at least one of the reactor conditions in the at least another of the reactors that receives the higher hydrocarbon stream.

32. The method of claim 31, wherein the higher hydrocarbons comprise ethane and at least one of the reactor conditions in the at least another of the reactors that receives the higher hydrocarbon stream is optimized to oxidatively dehydrogenate at least a portion of the ethane to produce ethylene.

33. The method of claim 32, wherein the separation unit is further configured to separate at least a portion of the ethane from the mixed hydrocarbon feed stream to produce a separated ethane stream and to feed the separated ethane stream to the at least another of the reactors that is optimized to oxidatively dehydrogenate at least a portion of the ethane to produce ethylene.

34. The method of claim 31, wherein the higher hydrocarbons comprise propane and at least one of the reactor conditions in the at least another of the reactors that receives the higher hydrocarbons is optimized to oxidatively dehydrogenate at least a portion of the propane to produce ethylene, propylene, or a mixture thereof.

35. The method of claim 34, wherein the separation unit is further configured to separate at least a portion of the propane from the mixed hydrocarbon feed stream to produce a separated propane stream and to feed the separated propane stream to the at least another of the reactors that is optimized to oxidatively dehydrogenate at least a portion of the propane to produce ethylene, propylene, or a mixture thereof.

36. The method of claim 20 wherein the oxygen transfer agent comprises at least one element selected from the group consisting of Mn, Fe, Mo, Ti, V, Pr, Cu, La, Ga and mixtures thereof.

37. The method of claim 36, wherein the oxygen transfer agent further comprises at least one promotor selected from the group consisting of alkaline metals, alkaline earth metals, boron, sulfur, salts of tungstic acid, salts of halides, and mixtures thereof.

38. The method of claim 20, wherein the oxygen transfer agent is selected from the group consisting of Li/Mn/B/MgO, Li/Mn/B/CaSO$_4$/MgO, Na/Pr$_6$O$_{11}$, and mixtures thereof.

39. A system for oxidative conversion of a mixed hydrocarbon feed stream to a product stream comprising at least one olefin, the system comprising:
  a plurality of reactors, each reactor in the plurality of reactors configured to:
  receive a portion of the mixed hydrocarbon feed stream,
  receive an oxidized oxygen transfer agent,
  oxidatively dehydrogenate at least a portion of at least one hydrocarbon in the mixed hydrocarbon feed stream at one or more reactor conditions in each reactor using the oxidized oxygen transfer agent to produce a portion of the product stream comprising the at least one olefin and a reduced oxygen transfer agent; and
  a regeneration unit in communication with at least one of the plurality of reactors and configured to:
  receive some or all of the reduced oxygen transfer agent,
  receive a gas comprising molecular oxygen,
  combine the reduced oxygen transfer agent and the gas to produce a recycled portion of the oxidized oxygen transfer agent, and
feed the recycled portion of the oxidized transfer agent to at least one reactor in the plurality of reactors;
wherein the at least one olefin comprises ethylene and;
wherein the mixed hydrocarbon feed stream comprises methane and propane and one or more of the reactor conditions in at least one of the reactors is optimized to oxidatively dehydrogenate and couple methane to produce at least a portion of the ethylene and one or more of the reactor conditions in another of the reactors is optimized to oxidatively dehydrogenate propane to produce at least another portion of the ethylene, and the one or more reactor conditions optimized to oxidatively dehydrogenate and couple methane to produce the at least a portion of the ethylene is different from the one or more reactor conditions optimized to oxidatively dehydrogenate propane to produce the at least another portion of the ethylene.

40. A method for oxidative conversion of a mixed hydrocarbon feed stream to a product stream comprising at least one olefin, the method comprising:
  receiving a portion of the mixed hydrocarbon feed stream into each reactor in a plurality of reactors,
  receiving an oxidized oxygen transfer agent into each reactor in the plurality of reactors, oxidatively dehydrogenating at least one hydrocarbon in the mixed hydrocarbon feed stream in each of the reactors at one or more reactor conditions in each reactor using the oxidized oxygen transfer agent in each of the reactors to produce a portion of the product stream comprising the at least one olefin and a reduced oxygen transfer agent in each of the reactors; and
  in a regeneration unit in communication with at least one reactor in the plurality of reactors:
  receiving some or all of the portions of the reduced oxygen transfer agent,
  receiving a gas comprising molecular oxygen,
  combining the reduced oxygen transfer agent and the gas thereby producing a recycled portion of the oxidized oxygen transfer agent, and
feeding the recycled portion of oxidized transfer agent to at least one reactor in the plurality of reactors;
wherein the at least one olefin comprises ethylene, and
wherein the mixed hydrocarbon feed stream comprises methane and propane and one or more of the reactor conditions in at least one of the reactors is optimized to oxidatively dehydrogenate and couple methane to produce at least a portion of the ethylene and one or more of the reactor conditions in another of the reactors is optimized to oxidatively dehydrogenate propane to produce another portion of the ethylene, and one or more of the reactor conditions optimized to oxidatively dehydrogenate and couple methane to produce the at least a portion of the ethylene is different from one or more of the reactor conditions optimized to oxidatively dehydrogenate propane to produce the at least another portion of the ethylene.

* * * * *